US00PP16734P2

(12) United States Plant Patent
Gossett

(10) Patent No.: US PP16,734 P2
(45) Date of Patent: Jun. 27, 2006

(54) ***TIARELLA* PLANT NAMED 'TNTIA041'**

(50) Latin Name: ***Tiarella* hybrid**
Varietal Denomination: TNTIA041

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 86 days.

(21) Appl. No.: 11/084,299

(22) Filed: Mar. 17, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—June Hwu
(74) *Attorney, Agent, or Firm*—Klarquist Sparkman, LLP

(57) ABSTRACT

A new and distinct cultivar of *Tiarella* plant characterized its compact habit with pink buds and very light purple flowers, and star-shaped leaves with dark speckling along the main veins.

1 Drawing Sheet

Botanical denomination: *Tiarella* hybrid.
Variety designation: TNTIA041.

BACKGROUND OF THE INVENTION

The present invention relates to a new and distinct cultivar of a hardy herbaceous perennial of the genus *Tiarella,* and known by the cultivar name 'TNTIA041'. The genus *Tiarella* is a member of the family Saxifragaceae.

The new cultivar originated as a cross between unknown parents. This new *Tiarella* was one of many seedlings grown from select, proprietary, interspecific hybrids that were unnamed, experimental varieties that were mass pollinated in the greenhouse in Canby, Oreg. As such no species designations are given.

SUMMARY OF THE INVENTION

This plant is characterized by the following:

1. Compact habit.
2. Attractive star-shaped leaf with dark speckling pattern along the main veins.
3. Pink buds and very light purple flower color.
4. Excellent vigor.

The new variety has been reproduced only by asexual propagation (division and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 is a picture of a one-and a half year old *Tiarella* 'TNTIA041' in bloom in the garden in late May in Canby, Oreg.

DETAILED PLANT DESCRIPTION

The following is a detailed description of the new *Tiarella* hybrid based on observations of three-year-old plants grown in the garden, in the ground, in shade, under typical outdoor conditions in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zones 4 to 9.
- *Form.*—Basal clump.
- *Size.*—38 cm. wide and 30 cm. high to the top of the foliage.
- *Vigor.*—Excellent.
- *Roots.*—Fibrous, freely branching, fine, and white in color, White 155A. Roots develop easily from divisions.

Foliage:
- *Type.*—Simple.
- *Arrangement.*—Rosette.
- *Shape.*—Ovate in outline.
- *Lobing.*—5 to 7 lobes cut to 1.5 to 2 cm above the petiole with terminal lobe the longest and prominent open spaces between the lobes. The sides of each lobe are almost parallel for most of their length.
- *Margins.*—Jagged, serrate.
- *Venation.*—Palmate.
- *Apex.*—Mucronulate.
- *Base.*—Cordate, not overlapping.
- *Blade length.*—Variable, grows to 14 cm.
- *Blade width.*—Variable, grows to 13 cm.
- *Surface texture.*—Hirsute top and bottom.
- *Petiole length.*—Variable, grows to 21 cm.
- *Petiole texture.*—Strongly pubescent.
- *Petiole color.*—Brown 200B overall.
- *Leaf color.*—Top side — Spring — between Yellow Green 144A and Green 138A with Greyed Purple 187A on the pattern. Summer and Winter — Yellow Green 146B with Brown 200A along main veins. Bottom side — Yellow Green 147B year round.

Inflorescence:

*Type.*—Raceme.

*Number of raceme in first spring flush.*—85.

*Flower number.*—60 per raceme.

*Bloom period.*—April to May with sporadic rebloom throughout the summer and fall.

*Peduncle.*—With 0 to 3 flowering branches. Height — 38 cm. Width — 2.5 mm at the widest point. Color — Brown 200C. Texture — Hispid.

*Pedicel.*—Size — 8 mm long and 1 mm wide. Texture — Glandular hairs. Color — Greyed Red 182B.

*Bloom time.*—April to May and sporadic bloom through the summer.

Flower bud:

*Size.*—4 mm deep and 2 mm wide.

*Description.*—Ovoid, downfacing unil open.

*Color.*—Pink, Greyed Purple 186D.

Flower:

*Type.*—Perfect, actinomorphic, sepals petaloid.

*Shape.*—Rotate.

*Petal and sepal number.*—5 petals, 5 fused sepals.

*flower size.*—8 mm wide and 5 mm deep including stamens.

*Petal shape.*—Lanceolate with a clawed base, margins entire, apex acute.

*Petal size.*—3 mm long and 1 mm wide.

*Petal color.*—White 155B on both sides.

*Calyx.*—Petaloid, parted almost to the base, lobes lanceolate, tips acute, margins entire, sepals 2 mm long and 1 mm wide, outside with purple tipped glandular hairs, inside glabrous.

*Calyx color.*—Very light purple, Purple 75D, slightly darker on outside.

*Stamens.*—10, conspicuously exerted.

*Filaments.*—White 155B, 3.5 mm long.

*Anthers undehisced.*—Orange Red 31B, 1.2 mm long.

*Pollen.*—Red Orange 32B, average amount.

*Pistil.*—White 155A overall with a few purple tipped glandular hairs on style, style 3 mm long.

*Fragrance.*—Slight.

Fruit:

*Type.*—A one-celled capsule, beak-like, composed of two unequal parts.

*Size.*—8 mm long.

*Color.*—Brown 200C.

Seeds:

*Color.*—Black 202A.

*Shape.*—Minute, oval, 1 mm long.

*Fertility.*—Fertile.

Disease and pest tolerance: This new hybrid shows good powdery mildew tolerance, the main problem for *Tiarella*. All *Tiarella* are susceptible to root weevils.

COMPARISONS WITH SIMILAR *TIARELLA*

Compared with *Tiarella* 'Spring Symphony' (U.S. Plant Pat. No. 12,397), *Tiarella* 'TNTIA041' has larger leaves that aren't as deeply divided. It has serrate margins, and a larger habit.

Compared to *Tiarella* 'Pink Bouquet' (an unpatented plant), the new variety has narrower leaf lobes, larger leaves, and a stronger pattern along the veins.

Compared with *Tiarella* 'Ninja' (U.S. Plant Pat. No. 11,168), *Tiarella* 'TNTIA041' has narrower leaf lobes, darker flowers, and the plant is more compact.

I claim:

1. A new and distinct cultivar of *Tiarella* plant substantially as illustrated and described.

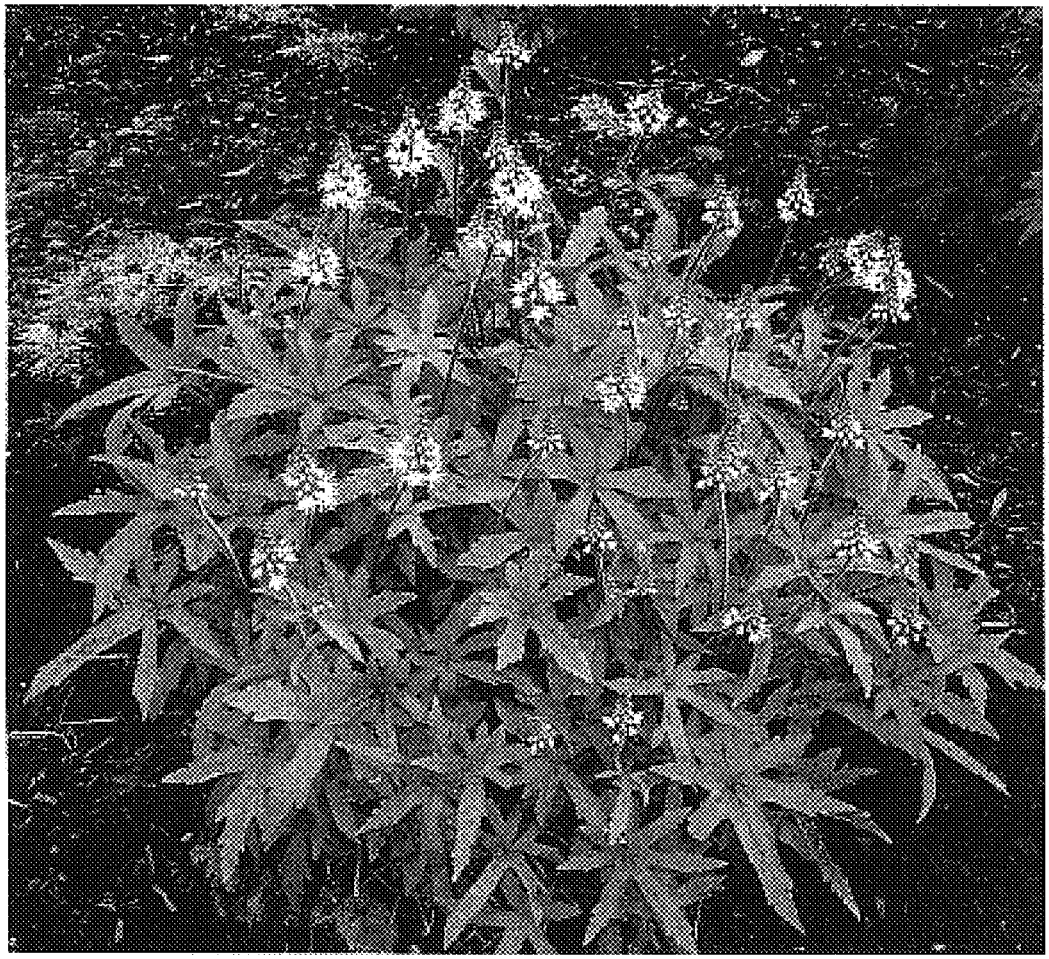

* * * * *